US012287618B2

(12) United States Patent
Kitamura et al.

(10) Patent No.: US 12,287,618 B2
(45) Date of Patent: Apr. 29, 2025

(54) MACHINING CENTER NC OPERATION PANEL WITH BODY TEMPERATURE MANAGEMENT FUNCTION

(71) Applicant: KITAMURA MACHINERY CO., LTD., Toyama (JP)

(72) Inventors: Akihiro Kitamura, Toyama (JP); Kosaku Kitamura, Toyama (JP); Toshihisa Tanada, Toyama (JP)

(73) Assignee: KITAMURA MACHINERY CO., LTD., Takaoka (JP)

( * ) Notice: Subject to any disclaimer, the term of this patent is extended or adjusted under 35 U.S.C. 154(b) by 421 days.

(21) Appl. No.: 17/786,763

(22) PCT Filed: Sep. 17, 2021

(86) PCT No.: PCT/JP2021/034271
§ 371 (c)(1),
(2) Date: Jun. 17, 2022

(87) PCT Pub. No.: WO2022/075042
PCT Pub. Date: Apr. 14, 2022

(65) Prior Publication Data
US 2023/0023522 A1    Jan. 26, 2023

(30) Foreign Application Priority Data
Oct. 8, 2020  (JP) ................................ 2020-170612

(51) Int. Cl.
*G05B 19/409* (2006.01)
*A61B 5/00* (2006.01)
(Continued)

(52) U.S. Cl.
CPC .......... *G05B 19/409* (2013.01); *A61B 5/0077* (2013.01); *A61B 5/015* (2013.01);
(Continued)

(58) Field of Classification Search
CPC ........ G05B 19/409; G05B 2219/36152; G05B 2219/36542; A61B 5/0077; A61B 5/015;
(Continued)

(56) References Cited

U.S. PATENT DOCUMENTS 4,999,614 A * 3/1991 Ueda .................... G08B 13/194
340/567
2012/0319847 A1  12/2012 Heller
(Continued)

FOREIGN PATENT DOCUMENTS

CN    110934572 A  *  3/2020
CN    111536377 A     8/2020
(Continued)

OTHER PUBLICATIONS

Search Report issued on Nov. 6, 2023 in corresponding European application No. 21877343.0.
(Continued)

*Primary Examiner* — Alicia M. Choi
(74) *Attorney, Agent, or Firm* — BACON & THOMAS, PLLC

(57) ABSTRACT

A machining center NC operation panel with a body temperature management function includes a visible range image camera and an infrared detection camera on a front surface of an operation panel. A storage unit has: an operator list; a face image file; and a body temperature management file for machine tool users and body-temperature managed users. A control unit includes: a face authentication processing unit; a work information processing unit that calls a work item assigned to the identified operator and displays it on a display unit of the operation panel so as to allow execution of a selection; and a body temperature acquisition processing unit that assesses whether or not the operator has a fever. When receiving a result of the assessment that the operator has a fever, the work information processing unit locks an operation screen of the display unit to inhibit continuation of an operation.

5 Claims, 8 Drawing Sheets

(51) Int. Cl.
  *A61B 5/01* (2006.01)
  *A61B 5/1171* (2016.01)
  *B23Q 15/12* (2006.01)

(52) U.S. Cl.
  CPC ............ *A61B 5/1176* (2013.01); *B23Q 15/12* (2013.01); *A61B 5/742* (2013.01); *A61B 2503/20* (2013.01); *G05B 2219/36152* (2013.01)

(58) Field of Classification Search
  CPC ... A61B 5/1176; A61B 5/742; A61B 2503/20; B23Q 15/12; B23Q 17/2438; B23Q 17/249; B23Q 1/0045; G06F 21/32; Y02P 90/02; G06Q 20/208
  See application file for complete search history.

(56) References Cited

U.S. PATENT DOCUMENTS

| | | | | |
|---|---|---|---|---|
| 2017/0011210 | A1* | 1/2017 | Cheong | A61B 5/681 |
| 2018/0000397 | A1* | 1/2018 | Sham | G08B 21/06 |
| 2019/0092337 | A1* | 3/2019 | Chua | B60W 30/14 |
| 2020/0033829 | A1 | 1/2020 | Kitamura et al. | |
| 2021/0358244 | A1* | 11/2021 | Chafni | G07C 9/257 |
| 2023/0419760 | A1* | 12/2023 | Chaurasia | G07C 9/20 |

FOREIGN PATENT DOCUMENTS

| | | |
|---|---|---|
| CN | 111 681758 A1 | 9/2020 |
| JP | 2008-226037 A | 9/2008 |
| JP | 2014-063423 A | 4/2014 |
| JP | 2018 38604 A | 3/2018 |
| JP | 6713688 B2 | 6/2020 |
| JP | 2021-064257 A | 4/2021 |
| WO | 2018 178444 A1 | 10/2018 |
| WO | 2020 050397 A1 | 3/2020 |
| WO | 2020 100223 A1 | 5/2020 |

OTHER PUBLICATIONS

Search Report dated Nov. 30, 2021, issued in corresponding PCT application No. PCT/JP2021/034271.
International Preliminary Examination dated Nov. 30, 2021, issued in corresponding PCT application No. PCT/JP2021/034271.

* cited by examiner

MACHINING CENTER NC OPERATION PANEL WITH BODY TEMPERATURE MANAGEMENT FUNCTION

TECHNICAL FIELD

The present invention relates to an NC (numerical control) operation panel that is connected to a machine tool body of a machining center, and performs numerical control, and specifically relates to an NC operation panel that has a function of facial authentication of an operator, and also body temperature management of the operator.

BACKGROUND ART

At a machining center, numerical control by an NC operation panel connected to a machine tool body enables implementation of various machining work as automated operation according to various types of NC program. Such an NC operation panel typically has a display section such as a display that is arranged in the upper section of the front face of the NC operation panel, and a CF card slot, and a USB port are installed around the display section. In addition, in the lower section, a keyboard on which various types of keys including a mouse pad, and mouse buttons are arranged, and furthermore a large number of operation-related switches, buttons, dials, and the like that are arranged thereon.

In addition, NC programs, tool information, and the like for various types of machining work are input to and accumulated in a storage section of a built-in control unit via the operation panel. Accordingly, an operator calls and executes a predetermined NC program by operating the NC operation panel, and thereby can cause the machine tool body to implement machining work as automated operation according to the NC program.

There are various levels of operators who engage in such an NC operation panel. Control functionalities, and types of work that should be permitted about the machine tool body are different among those operators depending on differences of work experience, and proficiency, differences of qualifications or the like. Because of this, it is necessary to restrict the range of controllable work items for each operator in terms of safety or security. In view of this, an individual identification system that identifies each operator at time of the start of work on an NC operation panel at a machining center, and makes only predetermined approved work items of each operator controllable is needed.

For example, the present inventors have already developed a machining center NC operation panel including an individual authentication system that can identify operators, and enforce favorable control restrictions (refer to Patent Literature 1). In this NC operation panel, facial image data of an operator captured by an imaging device mounted on the front face of the operation panel is compared with a facial image data group pre-registered in an operator list, and the operator is identified. Then, work information allocated to the identified operator is called, and only work items the operator is allowed to perform are displayed on a display section. That is, because only work that can be selected from the work items displayed on the display section can be executed, restrictions on the operator are enforced simply and conveniently, and surely, and the safety, and security of the machining center are ensured.

CITATION LIST

Patent Literatures

Patent Literature 1: Japanese Patent No. 6713688
Patent Literature 2: Japanese Unexamined Patent Application Publication No. 2018-38604

SUMMARY OF INVENTION

Technical Problem

However, in order to ensure the safety in operation control of the machining center, as a premise, the operator needs to be in a condition that she/he is capable of carrying out control the operation surely without mistakes even if the operation is restricted to only the allowed work items of the operator. For example, depending on the health condition such as a fever of the operator, there is a fear that the normal judgment is impaired, and it becomes difficult to perform correct operation control of the machining center.

In order to sense a deterioration of the health condition of an operator, and a risk of lowered concentration accompanying the deterioration, there is a machine safety apparatus that has been contrived such that vital signals such as heart rates, blood pressures, body temperatures, and brain waves are detected, monitored, and compared with reference values, and a machine tool is stopped in a case that the vital signals fall below the reference values (refer to Patent Literature 2, for example).

It should be noted that because such a safety apparatus based on a monitoring system is aimed to emergently stop a machine tool as a result of detection of a deteriorated condition of the health in the middle of work, measurement of vital signals of an operator by sensors is performed successively throughout the entire process period during the work. Because of this, the burden on the operator is not small. In addition, it is necessary to perform a measurement, and signal calculation process always, and moreover in a case that the work is stopped emergently in the middle of the process, the work process performed up to that point becomes wasted, and this increases costs on the apparatus side, and rather deteriorates the work efficiency.

In view of the problems described above, an object of the present invention is to provide a machining center NC operation panel with a body temperature management function that includes a body temperature measurement mechanism. Thereby, the machining center NC operation panel determines the physical condition of an operator before the start of work in accordance with a measured body temperature, restricts the start of work in a case that it is determined that the operator is in an inappropriate physical condition, and so can ensure higher safety, and eliminate waste of the work efficiency. In addition, the machining center NC operation panel can also perform body temperature management of workers, and the like at all times whether or not there is work.

Solution to Problem

In order to achieve the object described above, a machining center NC operation panel according to the invention described in claim 1 is a machining center NC operation panel which is a operation panel with an NC function that is connected to a machine tool body, and performs numerical control, the machining center NC operation panel including a control unit that is configured to drives a machining section of the machine tool body in accordance with a predetermined program, and a storage unit that stores various types of NC program, and tool information, and also including, on a front face of the operation panel, a display section, and an input section in which a large number of various types of key are arranged, the machining center NC operation panel including:

a visible region image camera that is mounted on the front face of the operation panel in a state that a visible light condensing lens is exposed, and captures a facial image of an operator; and an infrared ray detection camera that is mounted adjacent to the visible light condensing lens on the front face of the operation panel in a state that an infrared ray condensing lens is exposed, and, simultaneously with image-capturing by the visible region image camera, detects far infrared rays irradiated from a face surface of the operator, and obtains face surface temperature data, in which the storage unit stores:

an operator list including allocated work information that is created for each operator pre-registered as a machine tool user, the work information includes operations which the operators are respectively allowed to perform on the machine tool body and restricted operations which the operators are not respectively allowed to perform;

a facial image file storing a facial image data group of operators registered in the operator list; and a body temperature management file storing a body temperature database that is created for each operator pre-registered in the operator list, the body temperature database includes past body temperature measurement values of the operator and an average value of normal body temperatures based on the body temperature measurement values, the body temperature management file further holds a body temperature sub-database of an operator as a body temperature management user not registered as the machine tool users, the control unit includes:

a facial authentication processing unit configured to compare facial image data of the operator obtained by the visible region image camera with the facial image data group in the facial image file, search for a relevant person, and identify the operator;

a work information processing unit configured to call, from the operator list, work information allocated to the operator identified by the facial authentication processing unit, and display allowed work items of the operator selectably and executably on the display section on a basis of the work information; and a body temperature acquisition processing unit configured to acquire a body temperature measurement value of the operator from the face surface temperature data obtained by the infrared ray detection camera, display the body temperature measurement value on the display section, and also assess whether or not the operator has a fever on a basis of the body temperature measurement value, the body temperature acquisition processing unit is configured to have a work management mode and a body temperature management mode, the work management mode is executed when the operator whose body temperature is measured is identified as an operator pre-registered as a machine tool user in the operator list by the facial authentication processing section, a difference is computed by subtracting, from the body temperature measurement value, an average value of normal body temperatures included in a body temperature database of the operator stored in the body temperature management file;

in a case that the difference is greater than a predetermined threshold, it is assessed that the operator is in a fever condition, a signal representing a result of the assessment is output to the work information processing unit, and simultaneously the display section is caused to display an assessment screen representing that the operator is in a fever condition; and in a case that the difference is equal to or smaller than the predetermined threshold, it is assessed that the operator in a normal body temperature condition, a signal representing a result of the assessment is output to the work information processing unit, simultaneously the display section is caused to display an assessment screen representing that the operator is in a normal body temperature condition, and also the average value is updated by adding the body temperature measurement value to the body temperature database as a normal body temperature; and the body temperature management mode is executed in a case that the operator whose body temperature is measured is not identified as a machine tool user pre-registered in the operator list by the facial authentication processing unit, and when additionally it is confirmed that the operator is a body temperature management user whose body temperature sub-database is included in the body temperature management file;

a difference is computed by subtracting, from the body temperature measurement value, an average value of normal body temperatures included in the body temperature sub-database of the operator;

in a case that the difference is greater than the predetermined threshold, it is assessed that the operator is in a fever condition, and the display section is caused to display an assessment screen representing a result of the assessment; and in a case that the difference is equal to or smaller than the predetermined threshold, it is assessed that the operator is in a normal body temperature condition, the display section is caused to display an assessment screen representing a result of the assessment, and also the average value is updated by adding the body temperature measurement value to the body temperature sub-database as a normal body temperature, the work information processing unit is configured to have a function by which when a signal representing that the operator is in a normal body temperature condition is received from the body temperature acquisition processing unit, the display section is allowed to display the allowed work items of the operator, and when a signal representing that the operator is in a fever condition is received from the body temperature acquisition processing unit, the display section is caused to lock an operation screen, and prohibit continuation of operation for a start of work.

According to the configuration mentioned above, first, when an operator stands in front of the NC operation panel, a facial image can be captured by the visible region image camera on the operation panel front face, and identification of an individual pre-registered as a machine tool user is performed in accordance with a facial authentication process based on the facial image data. Then, only for an identified operator, the work information processing unit causes the display section to display allowed work items of the operator on the basis of work information of the operator stored in the operator list such that the allowed work items can be selected and executed. That is, only the allowed work items of the operator can be implemented, other unallowed work items are neither displayed on the display section nor executed, and so restrictions on the operator are enforced simply and conveniently, and surely. On the other hand, an unregistered operator is not identified in the facial authentication process, and no work items are displayed or executed. Due to such a facial authentication identification function, high safety, and security in the activation of the machining center are ensured.

In the present invention, simultaneously with image-capturing of a facial image by the visible region image camera, the infrared ray detection camera having the infrared ray condensing lens arranged on the operation panel front face adjacent to the visible light condensing lens of the visible region image camera detects far infrared rays irradiated from the face surface of the operator, and obtains temperature data of the face surface. Then, in a case that the operator is identified as a pre-registered machine tool user, the body temperature acquisition processing unit of the control unit executes the work management mode, acquires a body temperature measurement value from the face surface temperature data, and assesses the fever condition of the operator on the basis of the body temperature measurement value. The work information processing unit uses the result of the assessment for restrictions of work on the operator.

That is, if the body temperature acquisition processing unit assesses that the identified operator is in a normal body temperature condition, the display section is caused to display an assessment screen representing that the operator is in a normal body temperature condition, and in a case that the signal representing the result of the assessment that the operator is in a normal body temperature condition is received, the work information processing unit does not cause the display section to restrict continuation of screen operation by the operator. Accordingly, after checking the assessment screen, the operator who is assessed as being in a normal body temperature condition can continue screen control without problems, switch to a menu screen presenting her/his allowed work items, and select and execute a target work item.

In addition, in a case that the body temperature acquisition processing unit assesses that the identified operator is in a severe fever condition, the display section is caused to display an assessment screen representing that the operator is in a severe fever condition, and upon receiving a signal representing the result of the assessment that the operator has a severe fever, the work information processing unit locks the operation screen, and prohibits continuation of operation. Accordingly, the operator cannot continue screen operation on the locked assessment screen, and also cannot cause a menu screen presenting her/his allowed work items to be displayed. Thereby, it becomes impossible to execute any of the work items, and operation work of the machine tool is restricted surely.

Accordingly, it is possible to avoid a situation where the operator continues work in a poor physical condition that the operator lacks concentration or calm judgment due to a fever, and can make work mistakes, and so risks of occurrence of accidents, apparatus damage, and the like are solved before the start of work. Behavior of such a work management mode contribute to a further enhancement of the safety in the activation of the machining center. Note that the assessment screen representing a fever condition may also display a warning representing that continuation of operation is prohibited. This warning makes it easier for the operator to grasp her/his condition.

Then, according to the present invention, even if the operator is not pre-registered as a machine tool user, in the case that the operator has a body temperature sub-database as a body temperature management user in the body temperature management file, the body temperature acquisition processing unit, in the body temperature management mode, performs body temperature measurement and assessment at any time provided, and can perform body temperature management while accumulating and retaining body temperature measurement values, and additionally updating the average value of normal body temperatures. Typically, in some cases, there are various other types of equipment installed in a workshop, a factory or the like where the machining center is installed, and it is expected that there are not only operators who activate the machining center, but also various people around the machining center. Accordingly, the machining center NC operation panel can measure, on a daily basis and as body temperature management users, the body temperatures of even those people who do not activate the machining center, can check whether or not they have fevers, and can be used for ensuring the safety at work of each person.

Note that in a case that an operator to be a body temperature management user is not registered yet in the body temperature management file, in the body temperature management mode, if it is not confirmed that a body temperature sub-database of the operator is included in the body temperature management file, it is appropriate if the body temperature acquisition processing unit creates a body temperature sub-database of the operator by using the first body temperature measurement value when the first body temperature measurement and fever condition assessment are performed, in the body temperature management file, and registers the operator as a body temperature management user. Because at this time there is not the average value of normal body temperatures for assessment of the body temperature measurement value measured for the first time yet, it is simple and convenient to preset a body temperature reference value to be compared. In a case that the body temperature measurement value is greater than the body temperature reference value, the body temperature acquisition processing unit can assess that the operator is in a fever condition, and in a case that the body temperature measurement value is equal to or smaller than the body temperature reference value, the body temperature acquisition processing unit can assess that the operator is in a normal body temperature condition.

In the facial authentication process in the present invention, an existing facial authentication program can be adopted. Because it is expected that the target is relatively limited personnel who use the machining center, for example, it is sufficient to adopt a typical and widespread method in which feature point positions on a face such as the eyes, nose, corners of the mouth are detected in a facial image, and search, and collation are performed in the facial image data group to find data matching the feature point position data. Note that the visible region image camera for acquiring a facial image can include a small-sized camera including a solid-state image capturing element such as a CCD or a CMOS like ones built in various types of terminal equipment. Such a visible region image optical camera may be a single lens color camera, but, in another possible configuration, may be a so-called dual lens camera including two lenses to perform surer authentication. In this configuration, for example, if a color image, and a monochrome image are captured simultaneously, and the color image is compensated on the basis of light amount information obtained by the monochrome image-capturing, hues, and the contrast of an acquired synthesized image can be enhanced, also a clear image can be captured even at a relatively dark location, and so higher authentication precision can be attained.

In addition, it is sufficient if the infrared ray detection camera in the present invention is one that can sense far infrared rays emitted from the face surface of the operator, and measure the face surface temperature as the body temperature. Specifically, the infrared ray detection camera includes an infrared ray detection element that absorbs infrared rays received via a condensing lens, and generates an electric signal according to a temperature as the amount of infrared rays, and there are various methods depending on types of infrared ray detection element. For example, first, classifying roughly, there are thermal (non-quantum) detection elements that detect temperature changes that occur when infrared rays are absorbed as changes of resistance, and electromotive force, and quantum detection elements that sense infrared rays as light, and output electric signals by photoelectric conversion. It should be noted that the quantum detection elements require cooling, and have larger configurations corresponding to cooling mechanisms provided for the cooling; on the other hand, the thermal detection elements that do not require cooling are preferred because they can have smaller sizes.

Furthermore, such uncooled thermal infrared ray detection elements include thermopiles that use the thermoelectromotive force effect, thermistor bolometers that use the heat conduction effect, and pyroelectric elements that use the pyroelectric effect. Among them, bolometers can measure absolute temperatures without requiring temperature compensation, and so are more desirable in terms of simple and convenient configuration, and relatively low costs. Recently, a so-called thermal camera adopting a microbolometer focal plane array (FPA) formed by integrating heat sensitive elements including vanadium oxide or amorphous silicon by a micro-fabrication technology, and can obtain a temperature distribution image is used for body temperature measurement in general uses also.

In the present invention also, such a thermal camera method realized by an FPA that enables a size reduction at a relatively low cost may be adopted for the infrared ray detection camera. In this case, on the basis of the temperature distribution image data obtained from the infrared ray detection element, a temperature measurement value of the highest temperature distribution area which is equivalent to the forehead portion on the face surface can be acquired simply and conveniently as the body temperature measurement value.

Note that after the body temperature measurement, the display section displays an assessment screen representing the result of the assessment, and simultaneously may display a measured body temperature measurement value T. Furthermore, in a case that the operator whose body temperature is measured is identified as a machine tool user pre-registered in the operator list by the facial authentication processing unit, preferably, a registered facial image of the identified operator is also displayed as the authentication screen along with registration information such as a registration number or a name. The operator can easily check that the operator is authenticated unmistakably in accordance with the registration information like the registered facial image, and the registration number displayed on the authentication screen.

In addition, because a measurement value is accumulated in a body temperature database of each user at every instance of body temperature measurement after the database has been created, along with a newly measured body temperature measurement value, the body temperature acquisition processing unit may cause the display section to display a body temperature graph which is created from the newly measured body temperature measurement value, and latest past body temperature measurement values of measurement performed several times in the past from the body temperature database. In this case, in accordance with the displayed body temperature graph, the operator can check changes of her/his body temperature at a glance.

Note that it is sufficient if various types of screen such as the assessment screen displayed on the display section, the body temperature display screen presenting the body temperature measurement value T, and the body temperature graph, and also the authentication screen displaying the registration information are displayed simultaneously in a plurality of dialog box forms such as so-called message boxes or alarm boxes on the full background screen as the body temperature management screen. By this display form, the operator can grasp necessary information at once.

In the present invention, an assessment of the fever condition is made by using the average value of normal body temperatures as a reference value, and specifically body temperature measurement values that are obtained when the operator is assessed as being in a normal body temperature condition are accumulated, and the average value is updated. In view of this, if not only a body temperature graph like the one described above, but also the average value are displayed on the display section, the difference from a new body temperature measurement value can be grasped numerically also.

Note that when a body temperature database of a machine tool user is created, an initial reference value needs to be set. In view of this, when a machine tool user performs registration work by inputting work information, and the like to the operator list, the body temperature database can be created by inputting, as the initial reference value, a body temperature value that the operator is grasping, in everyday life, as a normal body temperature at time of a healthy condition. Alternatively, body temperature measurement is performed by using the infrared ray detection camera in the NC operation panel of the present invention when the operator is in a condition that she/he is surely healthy, and does not have a fever with no doubts, and the body temperature measurement value can be treated as the initial reference value.

In addition, whereas, in the assessment of the fever condition by the body temperature acquisition processing unit in the present invention, it is assessed that the operator is in a fever condition in a case that the difference obtained by subtracting the average value of normal body temperatures from the body temperature measurement value is greater than the predetermined threshold, and it is assessed that the operator is in a normal body temperature condition in a case that the difference is equal to or smaller than the predetermined threshold, it is expected that there is also a case that even if the operator is in a fever condition, she/he is in a mild fever condition which does not influence control work of the machine tool. In view of this, by using two levels of thresholds as the threshold to be used for the assessment, a specific distinction can be made between a mild fever condition and a severe fever condition that operation work should be prohibited immediately.

That is, as thresholds of at least the work management mode, the body temperature acquisition processing unit may have a first threshold to be compared first with the difference between the body temperature measurement value and the average value, and a second threshold which is greater than the first threshold, and is to be compared next with the difference in a case that the difference is greater than the first threshold. In the work management mode, in a case that the difference is greater than the first threshold, and equal to or smaller than the second threshold, a signal representing that the operator is in a mild fever condition can be output to the work information processing unit, and in a case that the difference is greater than the second threshold, a signal representing that the operator is in a severe fever condition that continuation of operation should be immediately prohibited can be output to the work information processing unit. Thereby, the work information processing unit can cause the display section to display a precautionary screen for checking the physical condition when receive the signal representing that the operator is in a mild fever condition. For example, in one possible manner, the first threshold is set to 1° C., and the second threshold is set to 2° C.

The operator who is assessed as being in a mild fever condition can also stop work with the machining center, and take a day off for the rest of the day, can also switch to other minor operation or alternatively can also stop work temporarily, and resume the machining center activation after a break. At time of the resumption, it is desirable if the body temperature is measured again. In view of this, preferably, the body temperature acquisition processing unit is further provided with a function to set a timer for performing body temperature measurement again after the passage of predetermined time in a case that the operator is assessed as being in a mild fever condition in the work management mode, and, at this time, causing the display section to display an instruction for body temperature re-measurement after several hours. Certainly, in the body temperature management mode also, two-level assessment using two thresholds may be performed in the same manner as in the work management mode.

In addition, by using two levels of body temperature reference values also in assessment of the first body temperature measurement value when a body temperature sub-database is created for a body temperature management user for the first time, a distinction can be made between a mild fever condition and a severe fever condition. For example, in one possible manner, the first body temperature reference value is set to 37.5° C., and the second body temperature reference value is set to 38.0° C.

Advantageous Effects of Invention

According to the machining center NC operation panel with a body temperature management function of the present invention, a machine tool user identified by the facial authentication based on a facial image captured at the visible region image camera is allowed to execute operation of only pre-allowed work items, and thereby restrictions on the operator are enforced simply and conveniently, and surely, and high safety, and security of the machining center is ensured. Additionally, in accordance with the body temperature measurement based on face surface temperature data detected at the infrared ray detection camera simultaneously with the image-capturing of the facial image, the fever condition of the operator is assessed, and restrictions of continuation of operation are enforced before the start of work. Accordingly, there are advantageous effects that a risk of execution of operation work of the machine tool by the operator in a poor physical condition due to a fever is avoided, and it is possible to attempt to further enhance the safety in machining center activation. Furthermore, in the present invention, the body temperature of an operator other than machine tool users is also measured as a body temperature management user, and assessment of the fever condition can be made. Accordingly, the present invention can be used for ensuring safety in work and operation by each of people who do not activate the machining center.

BRIEF DESCRIPTION OF DRAWINGS

FIG. 5 is a schematic diagram depicting examples of screens displayed on a display section after body temperature assessment, in which FIG. 5(a) is a body temperature management screen immediately after it is assessed that an operator is in a normal body temperature condition in a case that the operator is a machine tool user, and FIG. 5(b) is a dedicated menu screen presenting work items preset for the machine tool user displayed in accordance with screen operation after the body temperature management screen is displayed.

DESCRIPTION OF EMBODIMENTS

Figure 1:
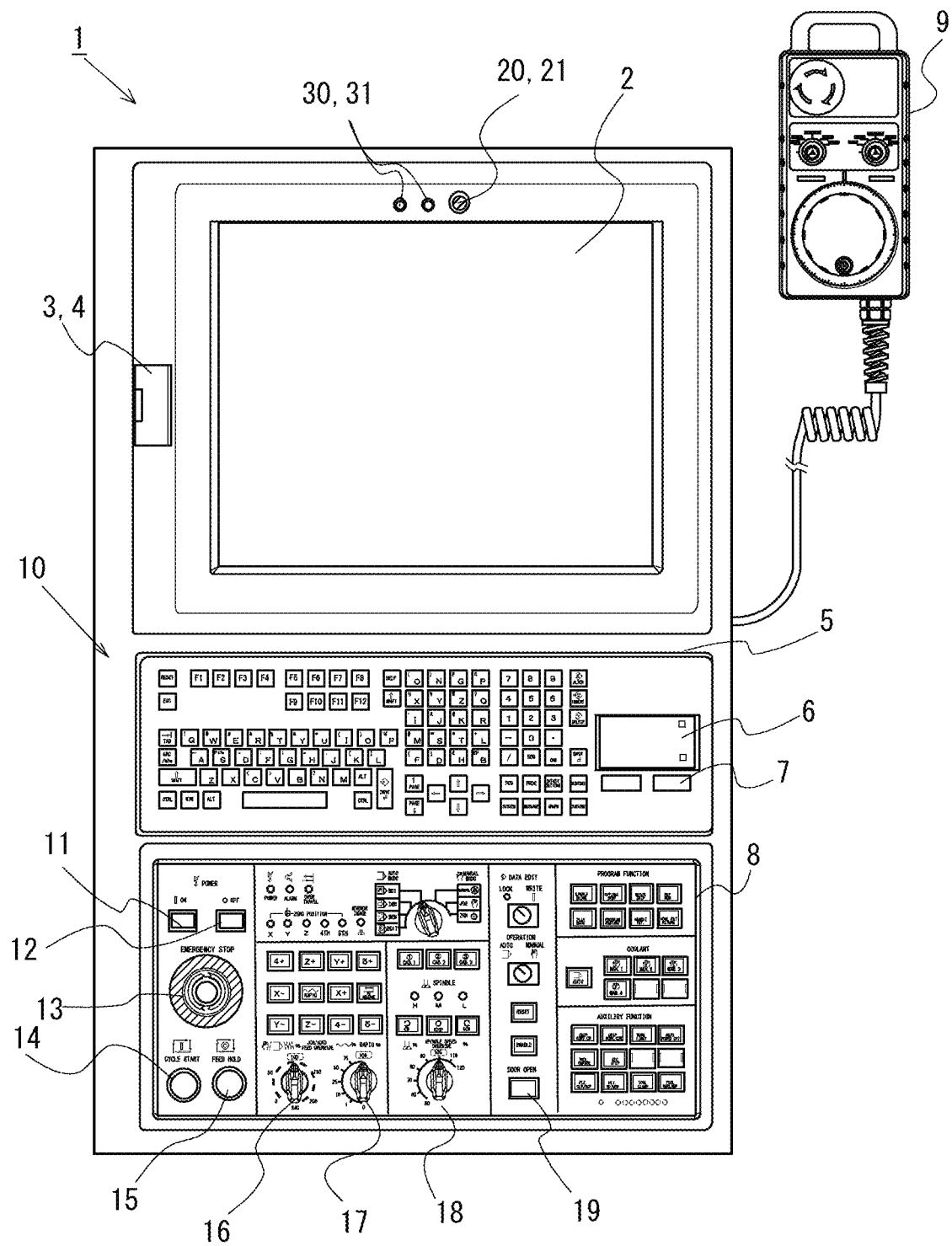
FIG. 1 is a schematic front view of a machining center NC operation panel with a body temperature management function according to one embodiment of the present invention.
Figure 2:
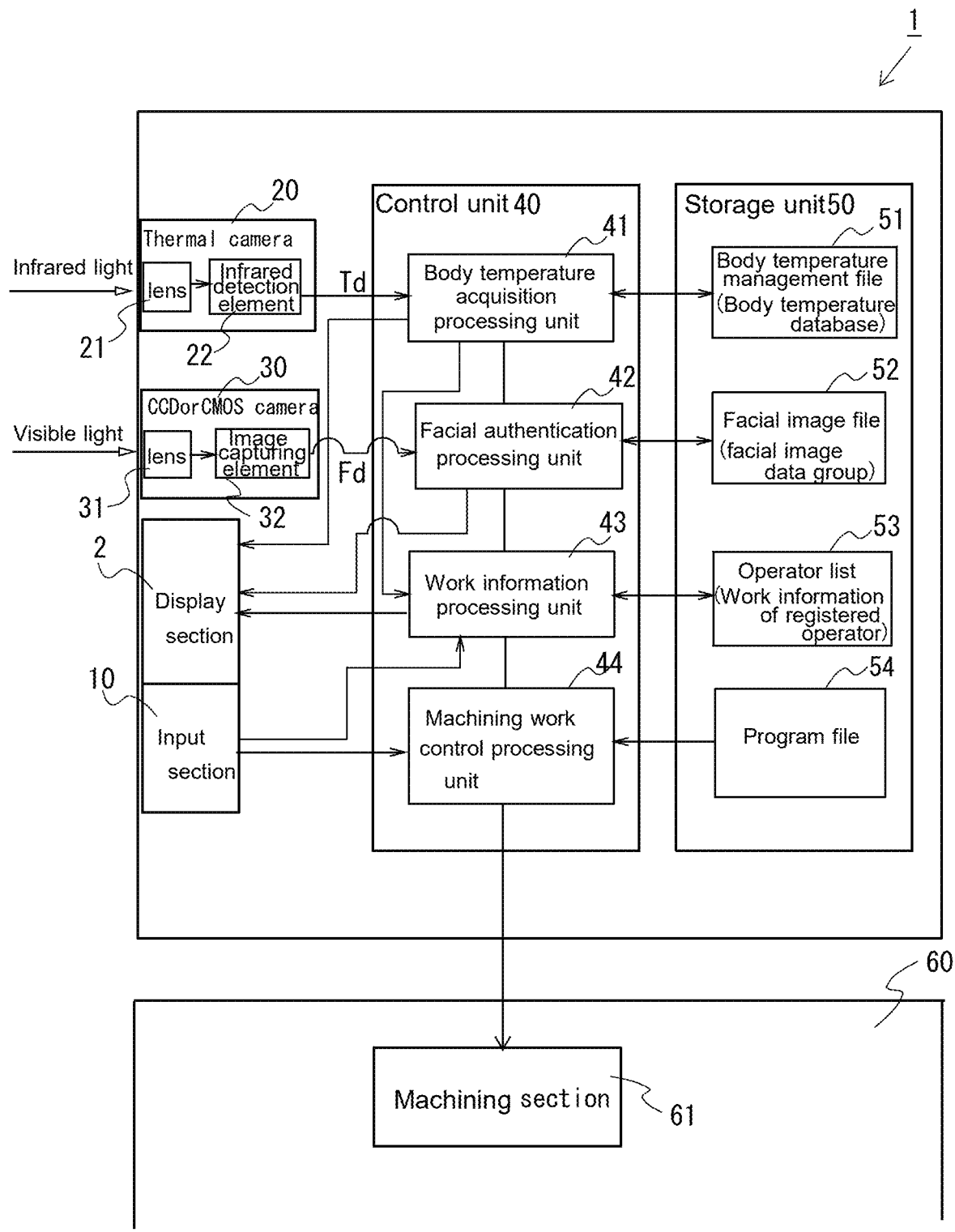
FIG. 2 is an internal conceptual diagram of the NC operation panel in FIG. 1.
Figure 3:
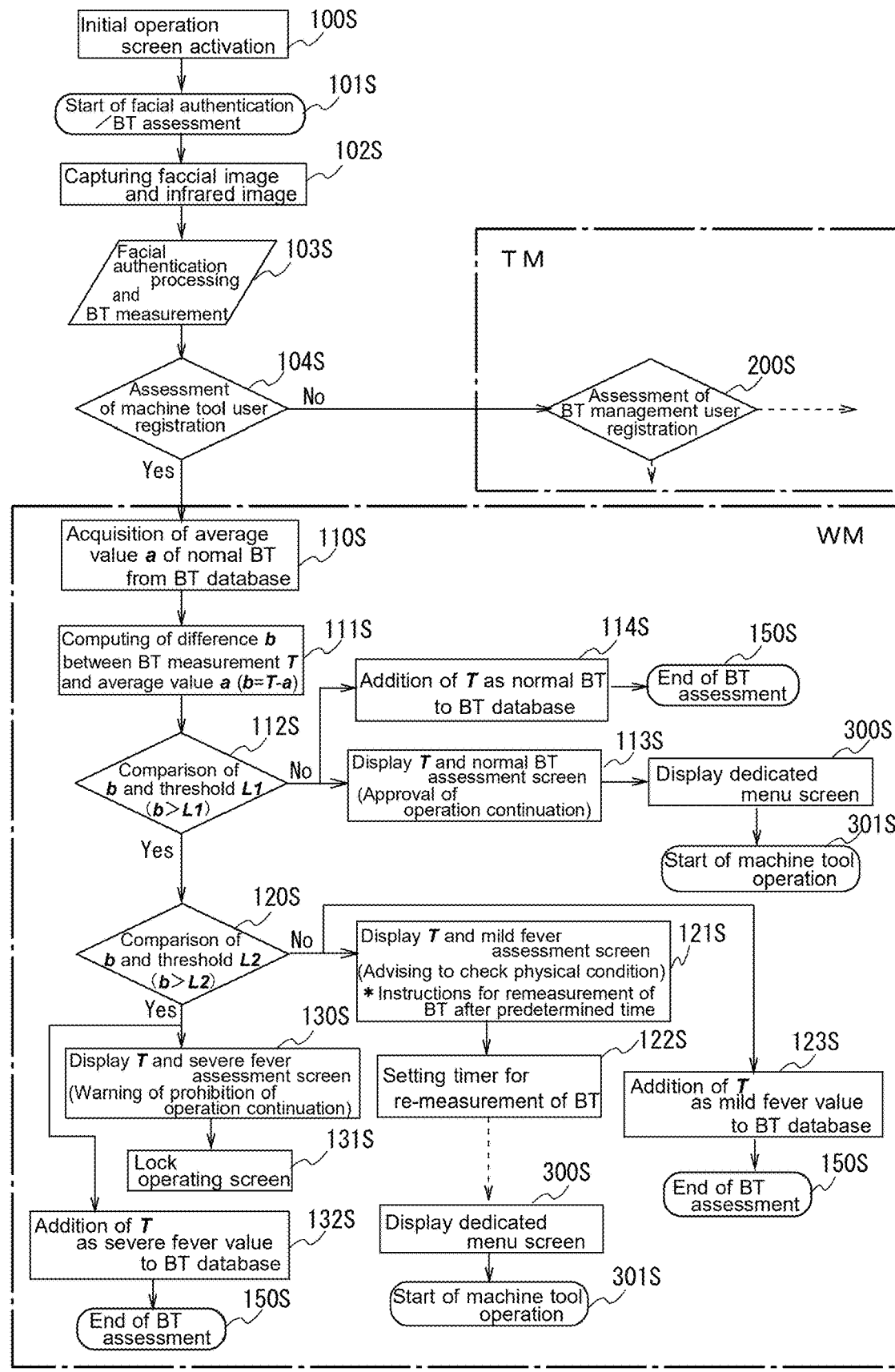
FIG. 3 is a flowchart for explaining mainly a work management mode in behavior processes at the NC operation panel in FIG. 1.
Figure 4:
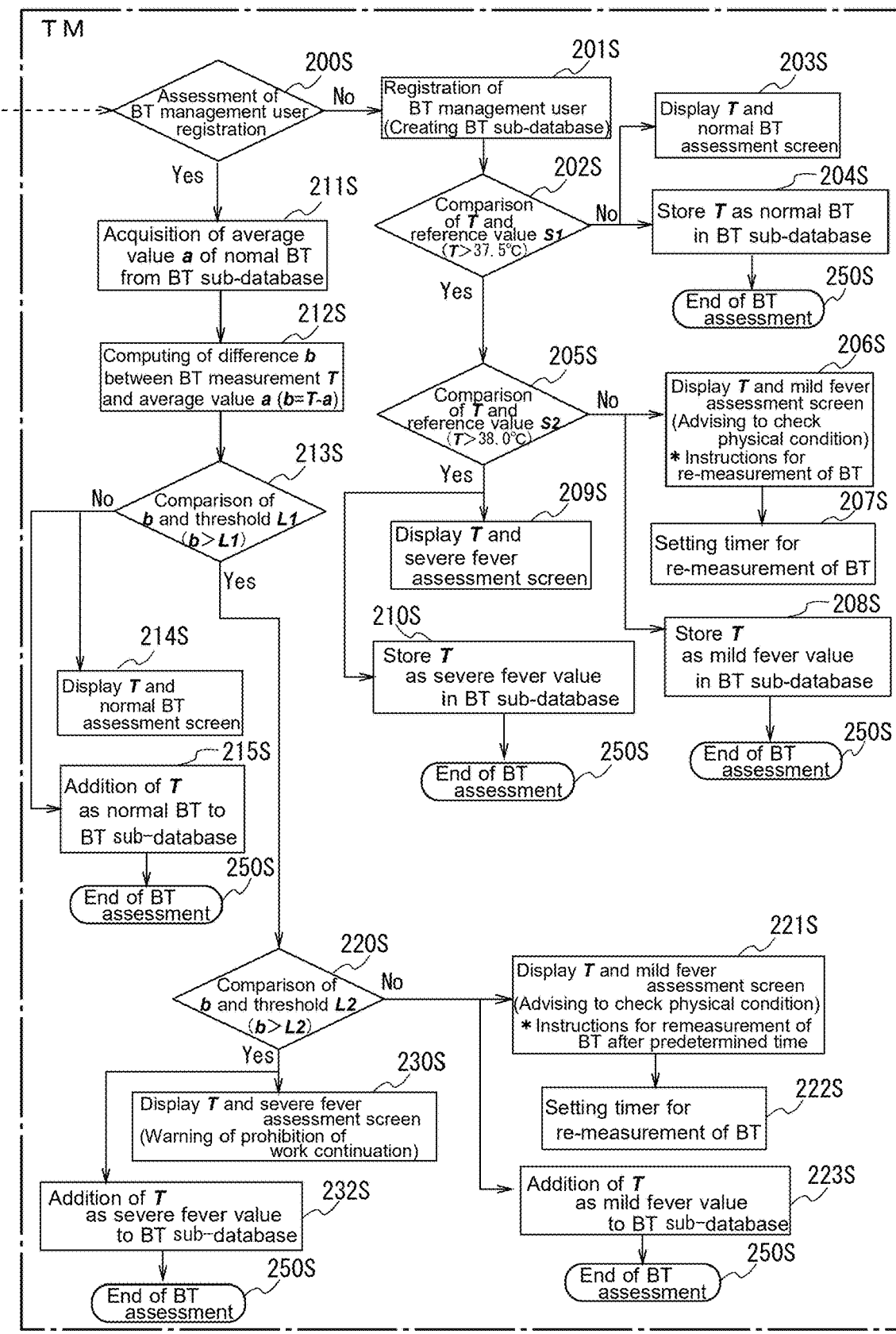
FIG. 4 is a flowchart for explaining mainly a body temperature management mode in the behavior processes at NC operation panel in FIG. 1.

A machining center NC operation panel with a body temperature management function according to one embodiment of the present invention is depicted in FIGS. 1, and 2. FIG. 1 is a schematic front view of the NC operation panel 1, and FIG. 2 is an internal conceptual diagram. In addition, FIG. 3, and FIG. 4 depict schematic flowcharts for explaining behavior processes in the NC operation panel 1.

Configuration of Machining Center NC Operation Panel with Body Temperature Management Function:

The NC operation panel 1 according to the present embodiment is connected to a machine tool body 60, and can cause a machining section 61 to perform NC program operation by numerical control. Accordingly, for example, the NC operation panel 1 is installed in proximity to the machine tool body 60 at a position such as a position adjacent to a control window on an exterior cover surrounding the machining section 61.

The basic configuration of the NC operation panel 1 is similar to the configuration of a conventional NC operation panel. That is, a display section 2 including a touch-panel liquid crystal screen or the like is provided in the upper area on the front face of the operation panel, and a CF card slot 3, and a USB port 4 are provided on the outer circumference of the display section 2 such that various types of data can be input and output. In addition, there is an input section 10 for manual input by an operator in an area below the display section 2, and a keyboard 5 including a mouse pad 6, and mouse buttons 7 is arranged first.

In an area further below the keyboard 5, a driving operation panel 8 on which various types of buttons, switch, and the like related to operation driving are arranged, is installed. For example, there are an operation preparation switch 11, an operation end switch 12, an emergency stop switch 13, an automated operation start switch 14, a feed hold switch 15, and the like. Still furthermore, a manual feed speed setting switch 16, a rapid feed override switch 17, a spindle speed override switch 18, an operation door interlock release button 19, and the like are arranged.

Then, in the present embodiment, a visible region image camera 30 for facial image acquisition having a visible light condensing lens 31 in an exposed state provided thereon is mounted on the front face of the NC operation panel 1 and near the middle of the upper portion of the frame section of the display section 2. Then, in addition, a thermal camera (infrared ray detection camera) 20 for body temperature measurement having an infrared ray condensing lens 21 in an exposed state provided thereon is mounted on the front face of the NC operation panel 1 and at a position adjacent to the visible light condensing lens 31 on the upper portion of the frame section of the display section 2.

For example, the visible region image camera 30 includes a CCD camera or a CMOS camera, and is configured to capture an image of the front face of an operator in a state that the operator is standing facing the display section 2, and output facial image data Fd from an image capturing element 32 to a control unit 40 inside the NC operation panel 1. Then, simultaneously, the thermal camera 20 receives, at an infrared ray detection element 22 including an uncooled microbolometer focal plane array, far infrared rays emitted from the face surface of the operator via the infrared ray condensing lens 21, and outputs temperature distribution image data Td of the face surface to the control unit 40.

In addition, the NC operation panel 1 has the control unit 40, and a storage unit 50 which are built-in sections, the control unit 40 drives the machining section 61 of the machine tool body 60 in accordance with a predetermined program, and causes the machining section 61 to perform NC program operation. At this time, various types of programs, and tool information stored in a program file 54 provided on the storage unit 50 can be read out and used.

In addition, the storage unit 50 has: a facial image file 52 storing a facial image data group of operators pre-registered as machine tool users; and an operator list 53 including allocated work information that is created for each registered machine tool user, and includes allowed operable work items, and unallowed operation-restricted work items of each machine tool user regarding the machine tool body 60.

In the present embodiment, the storage unit 50 further has a body temperature management file 51 storing a body temperature database that is created for each machine tool user, and the body temperature database stores and accumulates body temperature information and an average value a of normal body temperatures of the user, and data such as body temperature measurement values T or the average value a of normal body temperatures is updated at every instance of body temperature measurement mentioned later. In addition, the body temperature management file 51 also stores a body temperature sub-database created for each operator not registered as a machine tool user, but registered as a body temperature management user. Data in the body temperature sub-database of the body temperature management users is also updated at every instance of body temperature measurement.

The control unit 40 includes: a facial authentication processing unit 42 that compares facial image data of an operator obtained by the visible region image camera 30 with the facial image data group stored in the facial image file 52, searches for a relevant person, and identifies the operator; a work information processing unit 43 that calls, from the operator list 53, and processes work information allocated to the operator identified by the facial authentication processing unit 42, and, on the basis of the result of the process, causes the display section 2 to display a dedicated menu screen 80 that presents allowed work items of the operator such that the allowed work items can be selected and executed; and a machining work control processing unit 44 that calls, from the program file 54, a machining program according to a command based on a work item according to an input signal of selection operation about the work item on the dedicated menu screen 80, and outputs the machining program to the machine tool body 60. Because the operator can select and execute only the work items displayed on the dedicated menu screen 80 in accordance with the work information processing unit 43, work items that are not displayed, and are unallowed work items of the operator are neither selected nor executed, and work restrictions are enforced surely.

Furthermore, in the present embodiment, the control unit 40 includes a body temperature acquisition processing unit 41 that acquires the body temperature measurement value T of the operator on the basis of the temperature distribution image data Td of the face surface obtained by the thermal camera 20, assesses the fever condition of the operator on the basis of the body temperature measurement value T, and causes the display section 2 to display an assessment image representing the result of the assessment.

In the present embodiment, there are not only restrictions enforced by the work information processing unit 43 such that, for an operator registered as a machine tool user, only allowed work items of the operator are selected and executed on the basis of identification based on facial authentication at time of the start of work, but also assessment, based on a body temperature measurement value of the operator, in a work management mode WM by the body temperature acquisition processing unit 41 before the start of work as to whether or not the operator is in a condition that she/he can be approved to perform work. Accordingly, in a case that the operator as a machine tool user is in a severe fever condition that can lead to a lack of concentration or calm judgment, the work information processing unit 43 can prohibit continuation of operation on the basis of the result of the assessment, and so risks of occurrence of a work mistake by the operator, and damage or a malfunction of an apparatus accompanying the work mistake can be avoided.

Furthermore, the body temperature acquisition processing unit 41 also has a body temperature management mode TM in which the NC operation panel 1 performs body temperature measurement on a daily basis on an operator who does not use the machining center, and is not registered as a machine tool user, but is registered as a body temperature management user, and thereby it is possible to attempt to ensure the safety of work of the operator. This body temperature management mode TM can also cope with an operator who is not registered as a body temperature management user yet, by newly creating a body temperature sub-database in the body temperature management file 51 on the basis of the first body temperature measurement result.

Explanation of Behavior Processes of NC Operation Panel 1

Specific body temperature management behavior processes at the NC operation panel 1 with a body temperature (BT) management function according to the present embodiment are explained below along the flowcharts of FIGS. 3, and 4. Note that in the case depicted as an example here, two levels of thresholds, a first threshold L1, and a second threshold L2, are set as thresholds used for assessment of the fever condition. More specifically, the first threshold L1 is set to 1° C., and the second threshold L2 is set to 2° C.

In addition, FIGS. 5 to 10 are schematic diagrams depicting examples of body temperature management screens according to mutually different results of assessment displayed on the display section 2 after body temperature measurement. Note that the body temperature management screens in the present embodiment are configured to simultaneously display a body temperature display screen DA presenting the body temperature measurement value T and a body temperature graph G, an assessment screen DB representing the result of an assessment, and an authentication screen (DC, and DD) presenting a registered facial image 70F and registration number (70MU, and 70TU) of an operator, all of which are displayed in dialog box foams like message boxes on a single full background screen.

First, when an operator activates the NC operation panel 1 before the start of work, initial operation screen activation is performed at the display section 2 (100S). For example, when facial authentication/body temperature assessment (101S) is started in a state that the operator stands in front of the NC operation panel 1 on the basis of an instruction displayed on the initial control screen, and the face faces the visible light condensing lens 31, and infrared ray condensing lens 21 arranged near the middle of the upper portion of the frame section of the display section 2, the visible region image camera 30, and the thermal camera 20 capture a facial image/infrared ray image (102S).

The facial image data Fd obtained by the image-capturing by the visible region image camera 30 is output to the facial authentication processing unit 42 of the control unit 40, and the temperature distribution image data Td of the face surface obtained by the image-capturing by the thermal camera 20 is output to the body temperature acquisition processing unit 41 of the control unit 40. At the facial authentication processing unit 42, and the body temperature acquisition processing unit 41, a facial authentication process, and body temperature measurement are performed on the basis of the input data (Fd, and Td) (103S).

At the facial authentication processing unit 42, as the facial authentication process (103S), for example, features such as the arrangement of each facial part are extracted from the facial image data Fd, and the facial image data group stored in the facial image file 52 of the storage unit 50 is searched for data including matching features.

On the other hand, at the body temperature acquisition processing unit 41, as a process of the body temperature measurement (103S), the body temperature measurement value T of the operator is acquired on the basis of the temperature distribution image data Td obtained by the image-capturing by the thermal camera 20. For example, if it is supposed that the thermal camera 20 is a camera using an uncooled microbolometer focal plane array as the infrared ray detection element 22, distribution image data including absolute temperatures of the face surface is obtained as the temperature distribution image data Td. Accordingly, typically the forehead area is the highest temperature area, and so the highest temperature can be acquired simply and conveniently as the body temperature measurement value T.

In the facial authentication process, after the search for matching data in the facial image data group has ended, it is assessed whether or not there is machine tool user registration of the operator on the basis of the result of the search (104S). In a case that the operator is identified as a machine tool user as the result of the assessment, the body temperature acquisition processing unit 41 proceeds to the work management mode WM, and in a case that the operator is not identified as a machine tool user, the body temperature acquisition processing unit 41 proceeds to the body temperature management mode TM.

Work Management Mode WM

In the work management mode WM, the average value a of normal body temperatures is acquired from a body temperature database of the operator registered as a machine tool user stored in the body temperature management file 51 (110S), and the difference b (=T−a) between the body temperature measurement value T and the average value a is computed (111S). Then, the difference b, and the threshold L1 (=1° C.) are compared (112S). In a case that the difference b is smaller than the threshold L1=1° C., that is, in a case that the difference between the average value a of normal body temperatures of the operator and the body temperature measurement value T is equal to or smaller than 1° C., the body temperature acquisition processing unit 41 assesses that the operator is in a normal body temperature condition, causes the display section 2 to display the result of the assessment, and simultaneously outputs a signal representing the result of the assessment to the work information processing unit 43. The body temperature acquisition processing unit 41 creates the body temperature graph G using latest past body temperature measurement values of measurement performed multiple times that are accumulated in the body temperature database with the current body temperature measurement value T, and outputs the body temperature information to the display section 2 along with the body temperature measurement value T. Therefore, the display section 2 displays the body temperature measurement value T, and a normal body temperature assessment screen (113S).

More specifically, after the image-capturing of the facial image and the body temperature measurement, the display section 2 displays a body temperature management screen 70, and the body temperature display screen DA presenting the body temperature measurement value T and body temperature graph G of the body temperature information input from the body temperature acquisition processing unit 41 is displayed on the body temperature management screen 70. Simultaneously, the assessment screen DB presenting, to the operator, that the operator is in a normal body temperature condition is displayed on the body temperature management screen 70. In addition, in the configuration in the present embodiment, the authentication screen DC presenting the registered facial image 70F and machine tool user registration number 70MU of the operator along with the name is also displayed on the body temperature management screen 70.

Figure 5:
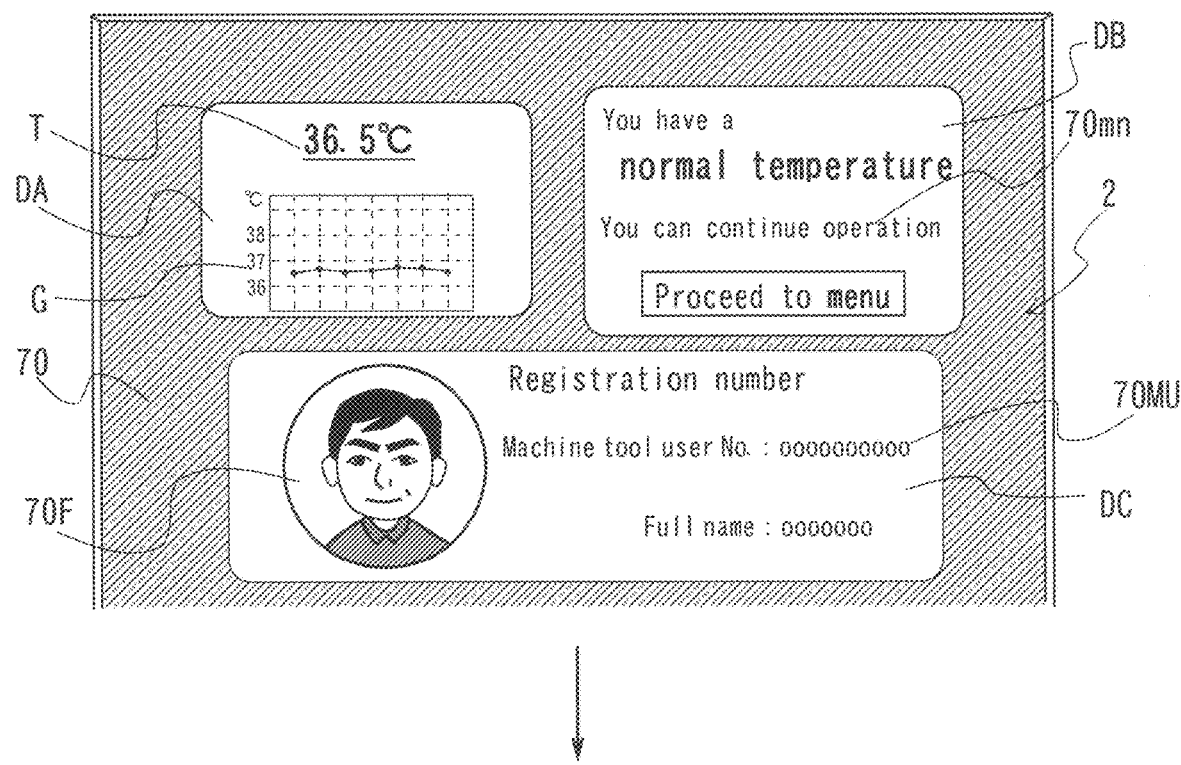
Figure 5:
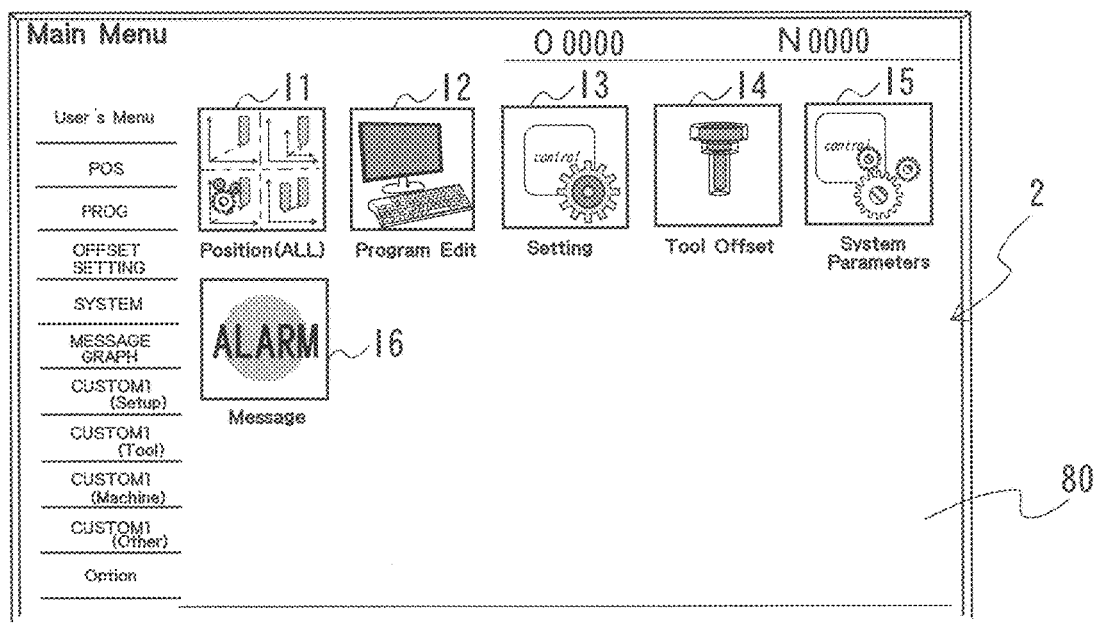

Accordingly, as depicted in (a) in FIG. 5, on the display section 2, the body temperature display screen DA presenting the current body temperature measurement value T and the body temperature graph G, the assessment screen DB presenting the result of the assessment of the body temperature measurement to the operator, and the authentication screen DC of the operator are displayed simultaneously on the same one body temperature management screen 70 like dialog boxes.

In a case that a normal body temperature assessment is made in the manner mentioned above, the body temperature acquisition processing unit 41 adds the currently acquired body temperature measurement value T, as a normal body temperature, to the body temperature database of the operator (114S), the average value a of normal body temperatures is updated, and the body temperature assessment ends (150S). On the other hand, upon receiving the signal representing a normal body temperature assessment result from the body temperature acquisition processing unit 41, the work information processing unit 43 determines that there are no problems even if the operator performs operation work of the machine tool, and permits continuation of operation, that is, enables the display the dedicated menu screen presenting pre-allowed work items of the operator as a machine tool user such that the work items can be selected and executed, without prohibiting the subsequent continuation of screen operation by the operator. Accordingly, after checking the assessment screen DB, the operator can perform screen operation, cause her/his dedicated menu screen to be displayed on the display section 2 (300S), and, as depicted in (b) in FIG. 5, select and execute a target item from the work items presented on the menu screen 80. Thereby, machine tool operation is started (301S).

Note that the body temperature acquisition processing unit 41 may cause the assessment screen DB to present not only the normal body temperature assessment information, but also a message 70*mn* representing that continuation of operation is allowed to the operator. In addition, the dedicated menu screen 80 displayed corresponding to the work information of the operator as a machine tool user displays icons of respective work items such as, for example, a "Current Position" icon I1 for transition to a coordinate screen, a "Program Edit" icon I2 for transition to a program edit screen, a "Setting" icon I3 for transition to a setting screen, a "Tool Offset" icon I4 for transition to an offset screen, a "System Parameters" icon I5 for transition to a system screen, and a "Message" icon I6 for transition to a message/tool path diagram screen. If, for example, program edit by the operator is not approved among them, the icon I2 is not displayed on the dedicated menu screen 80.

In addition, in a case that the difference b between the body temperature measurement value T and the average value a is greater than the threshold L1 as the result of the comparison between the difference b and the threshold L1 (112S), next, the difference b and the second threshold L2 (=2° C.) are compared (120S). In a case that the difference b is greater than the threshold L2=2° C., that is, in a case that the difference between the average value a of normal body temperatures of the operator and the body temperature measurement value T is greater than 2° C., the body temperature acquisition processing unit 41 assesses that the operator is in a severe fever condition, and causes the display section 2 to display the assessment screen DB representing the result of the assessment. Simultaneously, a signal representing the result of the assessment is output to the work information processing unit 43.

Figure 6:
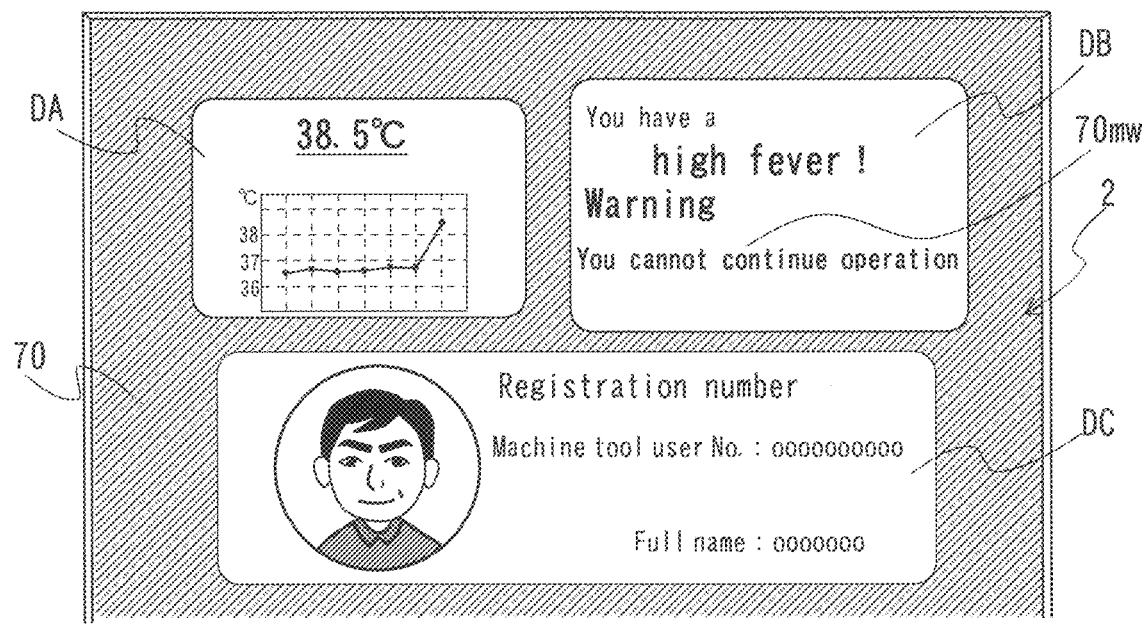
FIG. 6 is a schematic diagram depicting an example of a body temperature management screen displayed on the display section immediately after it is assessed that an operator is in a severe fever condition in a case that the operator is a machine tool user.

As depicted in FIG. 6, on the display section 2, the assessment screen DB presenting the result of the assessment that the operator is in a severe fever condition, and the authentication screen DC for the operator as a machine tool user are displayed on the body temperature management screen 70. Simultaneously, the body temperature acquisition processing unit 41 creates the body temperature graph G using latest past body temperature measurement values of measurement performed multiple times that are accumulated in the body temperature database with the current body temperature measurement value T, and causes the body temperature display screen DA presenting the body temperature graph G along with the body temperature measurement value T to be displayed on the body temperature management screen 70. Note that preferably the body temperature acquisition processing unit 41 causes the assessment screen DB to present not only the assessment information, but also a warning message 70*mw* representing that continuation of operation is prohibited.

In a case that a severe fever assessment is made in the manner mentioned above, the body temperature acquisition processing section 41 adds the currently acquired body temperature measurement value T, as a severe fever value, to the body temperature database of the operator (132S), and the body temperature assessment ends (150S). On the other hand, after the body temperature measurement value T and the severe fever assessment screen are displayed on the body temperature management screen 70 (130S), the work information processing unit 43 locks the operation screen (131S). Thereby, continuation of operation by the operator is prohibited, the display of the dedicated menu screen of the operator is disabled, and so further execution of work in a poor physical condition of the operator can be inhibited.

In addition, in a case that the difference b between the body temperature measurement value T and the average value a is compared with the threshold L2 (120S), and the difference b is smaller than the threshold L2=2° C., that is, in a case that the difference between the average value a of normal body temperatures of the operator and the body temperature measurement value T is greater than 1° C. and additionally is equal to or smaller than 2° C., the body temperature acquisition processing unit 41 assesses that the operator is in a mild fever condition, and causes the display section 2 to display the assessment screen DB representing the result of the assessment. Simultaneously, a signal representing the result of the assessment is output to the work information processing unit 43.

Figure 7:
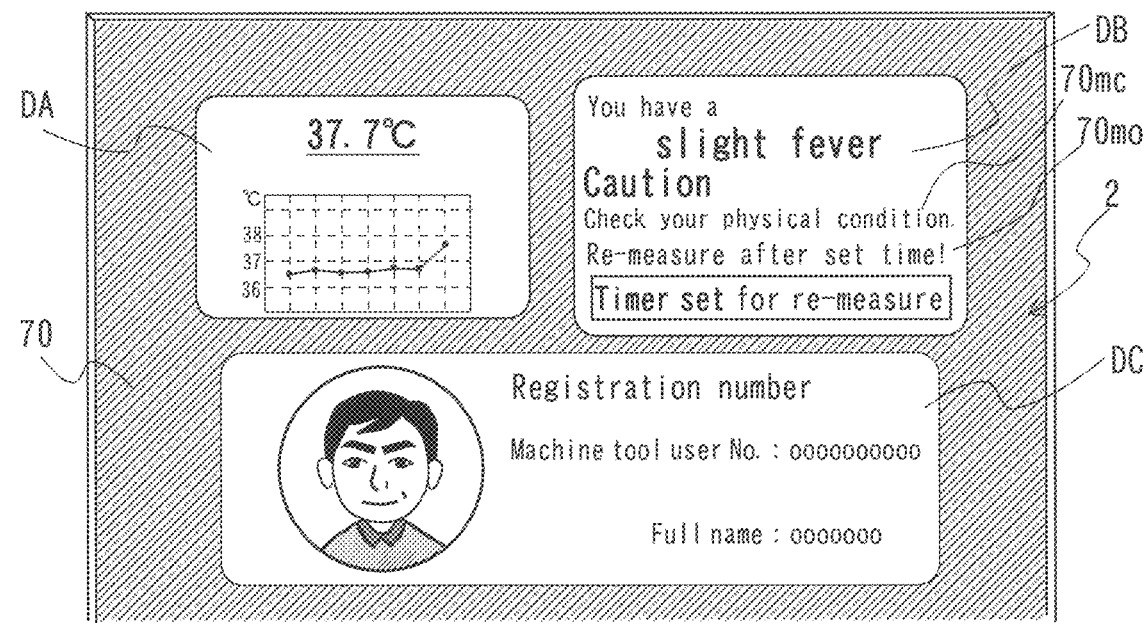
FIG. 7 is a schematic diagram depicting an example of a body temperature management screen displayed on the display section immediately after it is assessed that an operator is in a mild fever condition in a case that the operator is a machine tool user.

As depicted in FIG. 7, on the display section 2, the assessment screen DB presenting the result of the assessment that the operator is in a mild fever condition, and the authentication screen DC for the operator as a machine tool user are displayed on the body temperature management screen 70. Simultaneously, the body temperature acquisition processing unit 41 creates the body temperature graph G using latest past body temperature measurement values of measurement performed multiple times that are accumulated in the body temperature database with the current body temperature measurement value T, and causes also the body temperature display screen DA presenting the body temperature graph G along with the body temperature measurement value T to be displayed on the body temperature management screen 70. Note that preferably the body temperature acquisition processing unit 41 causes the assessment screen DB to present not only the assessment information, but also a precautionary message 70mc advising the operator to check the physical condition.

In a case that a mild fever assessment is made in the manner mentioned above, the body temperature acquisition processing unit 41 adds the currently acquired body temperature measurement value T, as a mild fever value, to the body temperature database of the operator (123S), and the body temperature assessment ends (150S). In the present embodiment, the body temperature measurement value T and the mild fever assessment screen are displayed on the body temperature management screen 70 (121S), simultaneously an instruction message 70mo instructing the operator to perform body temperature measurement again after predetermined time is displayed also, and a timer is set for a body temperature re-measurement time (122S). If the operator follows the instruction, and a normal body temperature assessment is made as the result of the body temperature re-measurement after the passage of the predetermined time, the operator can cause the dedicated menu screen to be displayed (300S), select and execute a desired work item, and proceed to the start of machine tool operation (301S). Certainly, if it is assessed that the operator is in a severe fever condition as the result of the temperature re-measurement, further execution of work is prohibited similarly to the process mentioned before.

Body Temperature Management Mode

In a case that the operator is not identified as a machine tool user pre-registered in the operator list 53 in the facial authentication process, the body temperature acquisition processing unit 41 proceeds to the body temperature management mode TM, and, as depicted in FIG. 4, first assesses whether or not the operator is registered as a body temperature management user (200S). That is, for example, a search is performed by using the name or the like of the operator to find out whether or not the body temperature management file 51 includes a body temperature sub-database which is given a registration number of the operator as a body temperature management user.

In a case that the operator is registered as a body temperature management user, a body temperature assessment is performed in accordance with processes similar to those in the work management mode mentioned before on the basis of the body temperature sub-database and the body temperature measurement value T. That is, first, the body temperature acquisition processing unit 41 acquires the average value a of normal body temperatures from the body temperature sub-database (211S), next computes the difference b between the body temperature measurement value T and the average value a (212S), compares the difference b with the first threshold L1, and the second threshold L2 stepwise, and assesses the fever condition. In the body temperature management mode TM, mainly, only the result of the assessment is displayed on the display section 2, and the work information processing unit 43 does not make the result of the assessment reflected in restrictions of operation of the machine tool.

Accordingly, first, the difference b and the threshold L1 are compared (213S). In a case that the difference b is equal to or smaller than the threshold L1, it is assessed that the operator has a normal body temperature, the display section 2 is caused to display the body temperature measurement value T and a normal body temperature assessment screen (214S), simultaneously the body temperature measurement value T is added to the body temperature sub-database as a normal body temperature (215S), and the body temperature assessment ends (250S).

Figure 8:
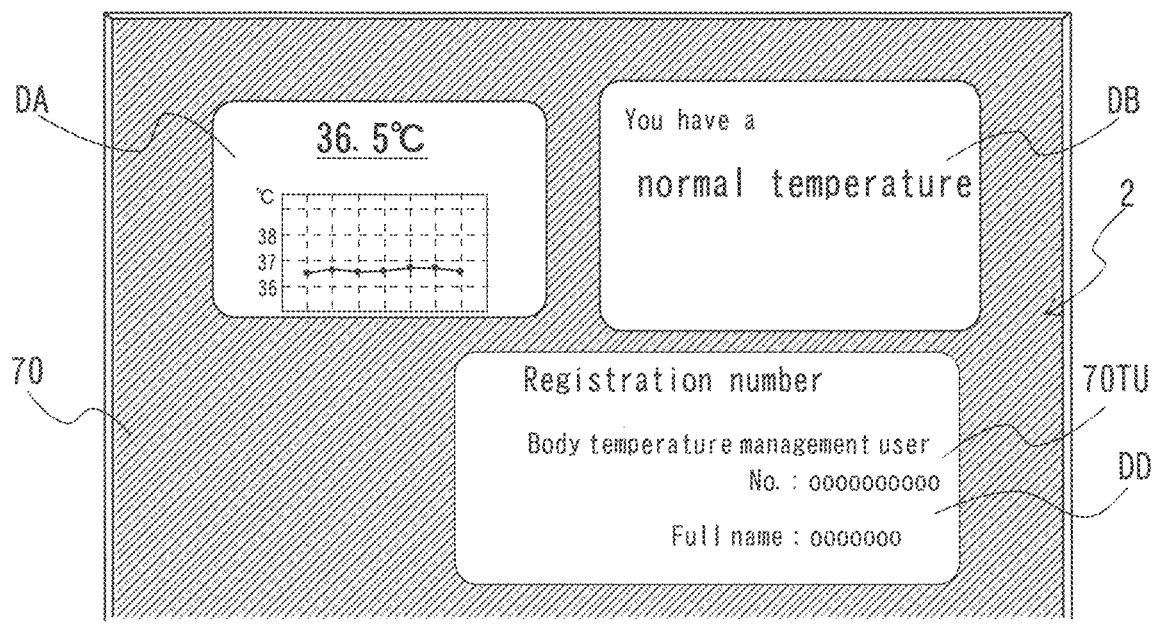
FIG. 8 is a schematic diagram depicting an example of a body temperature management screen displayed on the display section immediately after it is assessed that an operator is in a normal body temperature condition in a case that the operator is a body temperature management user.

In the present embodiment, as depicted in FIG. 8, similarly to the work management mode WM, screens displayed on the body temperature management screen 70 in the body temperature management mode TM are the body temperature display screen DA presenting the body temperature measurement value T and the body temperature graph G, the assessment screen DB presenting the result of the assessment, and the authentication screen DD of the operator. It should be noted that because facial image data of the operator as a machine tool user is not registered, the authentication screen DD does not present a registered facial image, but presents a registration number 70TU of the operator as a body temperature management user.

Figure 9:
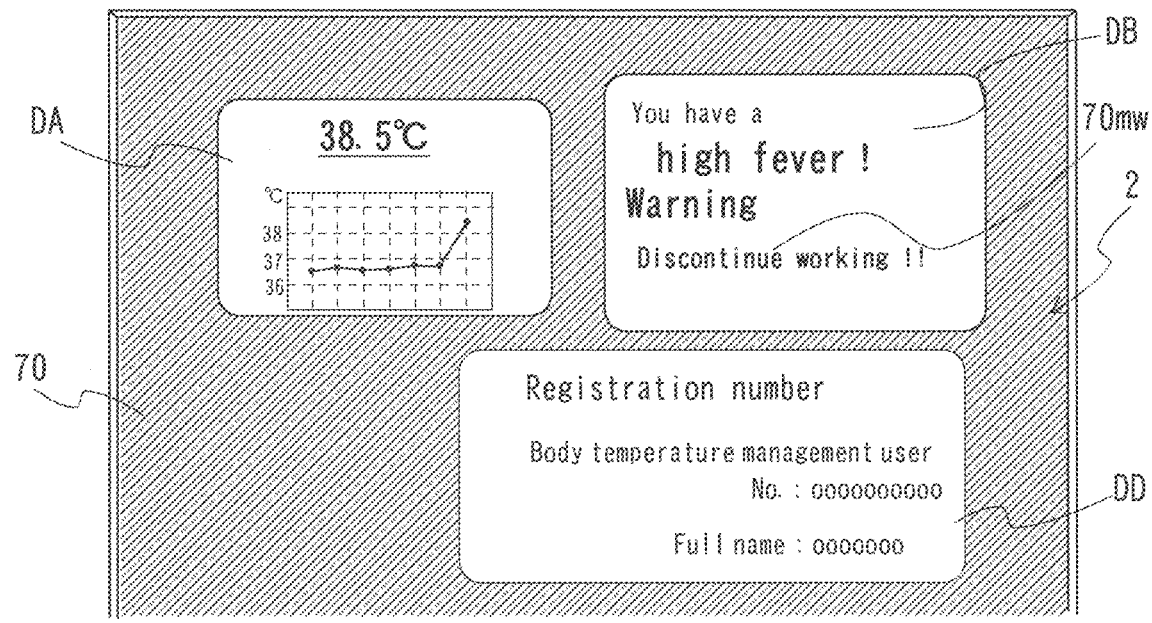
FIG. 9 is a schematic diagram depicting an example of a body temperature management screen displayed on the display section immediately after it is assessed that an operator is in a severe fever condition in a case that the operator is a body temperature management user.

In addition, in a case that the difference b is greater than the threshold L1 as the result of the comparison between the difference b and the threshold L1 (213S), the difference b and the second threshold L2 are compared (220S). Then, in a case that the difference b is greater than the threshold L2, the body temperature acquisition processing unit 41 assesses that the operator is in a severe fever condition, the display section 2 is caused to display the body temperature measurement value T and a severe fever assessment screen (230S), simultaneously the body temperature measurement value T is added to the body temperature sub-database as a severe fever value (232S), and the body temperature assessment ends (250S). As depicted in FIG. 9, on the display section 2, the body temperature display screen DA presenting the body temperature measurement value T and the body temperature graph G, the assessment screen DB, and the authentication screen DD are displayed simultaneously on the same one body temperature management screen 70. In the case of the severe fever assessment, preferably, the assessment screen DB presents the warning message 70mw like one advising the operator to stop operation, and go home.

In addition, in a case that the difference b is equal to or smaller than the threshold L2 as the result of the comparison between the difference b and the second threshold L2 (220S), the body temperature acquisition processing unit 41 assesses that the operator is in a mild fever condition, the display section 2 is caused to display the body temperature measurement value T and a mild fever assessment screen (221S), simultaneously the body temperature measurement value T is added to the body temperature sub-database as a mild fever value (223S), and the body temperature assessment ends (250S). On the display section 2, the body temperature display screen DA presenting the body temperature measurement value T and the body temperature graph G, the assessment screen DB, and the authentication screen DD are displayed simultaneously on the same one body temperature management screen 70. At this time, preferably, the assessment screen DB is caused to present also a precautionary message advising the operator to check the physical condition. In addition, along with the display of the mild fever assessment screen, an instruction message for instructing the operator to perform body temperature measurement again after predetermined time may be displayed also, and a timer for a body temperature re-measurement time after several hours may be set (222S).

Note that in a case that the operator is not registered as a body temperature management user yet, the body temperature acquisition processing unit 41 creates, in the body temperature management file 51, a body temperature sub-database of the operator on the basis of the first body temperature measurement value T, and registers the operator as a body temperature management user (201S). Specifically, first, a body temperature sub-database which is given a registration number of the operator as a body temperature management user is created for the operator.

Then, because there is not the average value of normal body temperatures for assessment yet, the body temperature measurement value T that is measured for the first time is compared with predetermined body temperature reference values. In the present embodiment, two levels of thresholds, a first reference value S1 and a second reference value S2, are set as the body temperature reference values. For example, the first reference value S1 is set to 37.5° C., and the second reference value S2 is set to 38.0° C.

Figure 10:
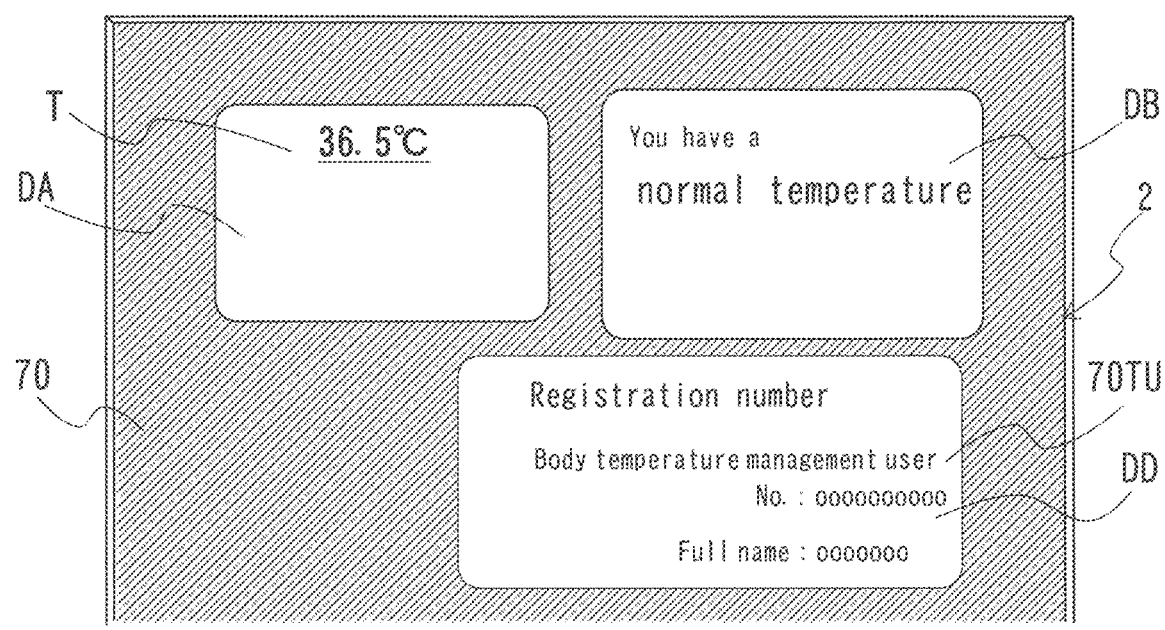
FIG. 10 is a schematic diagram depicting an example of a body temperature management screen displayed on the display section immediately after it is assessed that an operator is in a normal body temperature condition in a case that the operator is a body temperature management user whose body temperature is measured for the first time.

Accordingly, the body temperature acquisition processing unit 41 first compares the body temperature measurement value T and the first reference value S1 (202S). In a case that the body temperature measurement value T is equal to or smaller than the reference value S1 (37.5° C.) as a result, it is assessed that the operator is in a normal body temperature condition, and the body temperature measurement value T and a normal body temperature assessment screen are displayed on the body temperature management screen 70 of the display section 2 (203S). At this time, as depicted in FIG. 10, along with the assessment screen DB, the authentication screen DD, and the body temperature display screen DA are displayed simultaneously, but because there is no past data of body temperature measurement values, the body temperature display screen DA does not present the body temperature graph G, but presents only the body temperature measurement value T. The body temperature measurement value T is stored in the body temperature sub-database as a normal body temperature (204S), and the body temperature assessment ends (250S).

In addition, in a case that the body temperature measurement value T is greater than the reference value S1 (37.5° C.) as the result of the comparison between the body temperature measurement value T and the first reference value S1 (202S), the body temperature measurement value T and the second reference value S2 are compared (205S). If the body temperature measurement value T is equal to or smaller than the reference value S2 (38.0° C.), the body temperature acquisition processing unit 41 assesses that the operator is in a mild fever condition, and causes the body temperature measurement value T and a mild fever assessment screen to be displayed on the body temperature management screen 70 of the display section 2 (206S). The body temperature measurement value T is stored in the body temperature sub-database as a mild fever value (208S), and the body temperature assessment ends (250S). In addition, along with the display of the mild fever assessment screen, an instruction message for instructing the operator to perform body temperature measurement again after predetermined time may be displayed also, and a timer for a body temperature re-measurement time after several hours may be set (207S).

In addition, in a case that the body temperature measurement value T is greater than the second reference value S2, the body temperature acquisition processing unit 41 assesses that the operator is in a severe fever condition, and causes the body temperature measurement value T and a severe fever assessment screen to be displayed on the body temperature management screen 70 of the display section 2 (209S). The body temperature measurement value T is stored in the body temperature sub-database as a severe fever value (210S), and the body temperature assessment ends (250S). Note that it is desirable if the assessment screen presenting the severe fever assessment also presents a warning message advising the operator to stop work and operation.

As described above, in the present embodiment, even the body temperature of an operator who does not use the machining center can be measured on a daily basis by the NC operation panel as the body temperature of a body temperature management user, and so management can be carried out to ensure safety on the basis of the result of an assessment of the fever condition based on the body temperature measurement value T.

Note that layouts such as the arrangement, type or content presentation expression of each dialog box screen on a body temperature management screen depicted in the embodiment mentioned above are disclosed as examples, and the present invention is not limited by the layouts.

LIST OF REFERENCE SIGNS

1: NC operation panel
2: Display section
3: CF card slot
4: USB port
5: Keyboard
6: Mouse pad
7: Mouse button
8: Driving operation panel
9: Manual pulse generator
10: Input section
11: Operation preparation switch
12: Operation end switch
13: Emergency stop switch
14: Automated operation start switch
15: Feed hold switch
16: Manual feed speed setting switch
17: Rapid feed override switch
18: Spindle speed override switch
19: Operation door interlock release button
20: Thermal camera (infrared ray detection camera)
21: Infrared ray condensing lens
22: Infrared ray detection element
30: Visible region image camera
31: Visible light condensing lens
32: Image capturing element (CCD or CMOS)
40: Control unit
41: Body temperature acquisition processing unit
WM: Work management mode
TM: Body temperature management mode
42: Facial authentication processing unit
43: Work information processing unit
44: Machining work control processing unit
50: Storage unit
51: Body temperature management file
52: Facial image file
53: Operator list
54: Program file
60: Machine tool body
61: Machining section
70: Body temperature management screen
70F: Registered facial image
DA: Body temperature display screen
T: Body temperature measurement value
G: Body temperature graph DB: Assessment screen
70mn, 70mc, 70mo, 70mw: Message
DC, DD: Authentication screen
70MU: Registration number (machine tool user)
70TU: Registration number (body temperature management user)
80: Dedicated menu screen
I1, I2, I3, I4, I5, I6: Work item icon

The invention claimed is:

1. A machining center NC (Numerical Control) operation panel which is an operation panel with an NC function that is connected to a machine tool body, and performs numerical control, the machining center NC operation panel including a control unit that is configured to drive a machining section of the machine tool body in accordance with a predetermined program, and a storage unit that stores various types of NC program, and tool information, and also including, on a front face of the operation panel, a display section, and an input section in which a large number of various types of key are arranged, the machining center NC operation panel including:

a visible region image camera that is mounted on the front face of the operation panel in a state that a visible light condensing lens is exposed, and captures a facial image of an operator; and an infrared ray detection camera that is mounted adjacent to the visible light condensing lens on the front face of the operation panel in a state that an infrared ray condensing lens is exposed, and, simultaneously with image-capturing by the visible region image camera, detects far infrared rays irradiated from a face surface of the operator, and obtains face surface temperature data, wherein the storage unit stores:

an operator list including allocated work information that is created for each operator pre-registered as a machine tool user, the work information includes operations which the operators are respectively allowed to perform on the machine tool body and restricted operations which the operators are not respectively allowed to perform;

a facial image file storing a facial image data group of operators registered in the operator list; and a body temperature management file storing a body temperature database that is created for each operator pre-registered in the operator list, the body temperature database includes past body temperature measurement values of the operator and an average value of normal body temperatures based on the body temperature measurement values, the body temperature management file further retains a body temperature sub-database of an operator as a body temperature management user not registered as the machine tool users, the control unit includes:

a facial authentication processing unit configured to compare facial image data of the operator obtained by the visible region image camera with the facial image data group in the facial image file, search for a relevant person, and identify the operator;

a work information processing unit configured to call, from the operator list, work information allocated to the operator identified by the facial authentication processing unit, and display allowed work items of the operator selectably and excutably on the display section on a basis of the work information; and a body temperature acquisition processing unit configured to acquire a body temperature measurement value of the operator from the face surface temperature data obtained by the infrared ray detection camera, display the body temperature measurement value on the display section, and also assess whether or not the operator has a fever on a basis of the body temperature measurement value, the body temperature acquisition processing unit is configured to have a work management mode and a body temperature management mode, the work management mode is executed when the operator whose body temperature is measured is identified as an operator pre-registered as a machine tool user in the operator list by the facial authentication processing section, a difference is computed by subtracting, from the body temperature measurement value, an average value of normal body temperatures included in a body temperature database of the operator stored in the body temperature management file;

in a case that the difference is greater than a predetermined threshold, it is assessed that the operator is in a fever condition, a signal representing a result of the assessment is output to the work information processing unit, and simultaneously the display section is caused to display an assessment screen representing that the operator is in a fever condition; and in a case that the difference is equal to or smaller than the predetermined threshold, it is assessed that the operator in a normal body temperature condition, a signal representing a result of the assessment is output to the work information processing unit, simultaneously the display section is caused to display an assessment screen representing that the operator is in a normal body temperature condition, and also the average value is updated by adding the body temperature measurement value to the body temperature database as a normal body temperature; and the body temperature management mode is executed in a case that the operator whose body temperature is measured is not identified as a machine tool user pre-registered in the operator list by the facial authentication processing unit, and when additionally it is confirmed that the operator is a body temperature management user whose body temperature sub-database is included in the body temperature management file;

a difference is computed by subtracting, from the body temperature measurement value, an average value of normal body temperatures included in the body temperature sub-database of the operator;

in a case that the difference is greater than the predetermined threshold, it is assessed that the operator is in a fever condition, and the display section is caused to display an assessment screen representing a result of the assessment; and in a case that the difference is equal to or smaller than the predetermined threshold, it is assessed that the operator is in a normal body temperature condition, the display section is caused to display an assessment screen representing a result of the assessment, and also the average value is updated by adding the body temperature measurement value to the body temperature sub-database as a normal body temperature, the work information processing unit is configured to have a function by which when a signal representing that the operator is in a normal body temperature condition is received from the body temperature acquisition processing unit, the display section is allowed to display the allowed work items of the operator, and when a signal representing that the operator is in a fever condition is received from the body temperature acquisition processing unit, the display section is caused to lock an operation screen, and prohibit continuation of operation for a start of work.

2. The machining center NC operation panel with a body temperature management function according to claim 1, wherein, in the body temperature management mode, when the operator whose body temperature is measured is not identified as a machine tool user pre-registered in the operator list by the facial authentication processing section, additionally a body temperature sub-database of the operator is not included in the body temperature management file, and the operator is not identified also as a body temperature management user:

the acquired body temperature measurement value is compared with a predetermined body temperature reference value;

in a case that the body temperature measurement value is greater than the body temperature reference value, it is assessed that the operator is in a fever condition, and the display section is caused to display an assessment unit representing a result of the assessment; and in a case that the body temperature measurement value is equal to or smaller than the body temperature reference value, it is assessed that the operator is in a normal body temperature condition, the display section is caused to display an assessment screen representing a result of the assessment, and a body temperature database of the operator as a body temperature management user is created in the body temperature management file on a basis of the body temperature measurement value.

3. The machining center NC operation panel with a body temperature management function according to claim 1, wherein the body temperature acquisition processing unit is configured to have a function by which, in the work management mode, in a case that the operator whose body temperature is measured is identified as a machine tool user pre-registered in the operator list by the facial authentication processing section, the display section is further caused to display an authentication screen presenting registration information including a registered facial image of the operator on a basis of a result of the identification.

4. The machining center NC operation panel with a body temperature management function according to claim 1, wherein the body temperature acquisition processing unit is configured to have a function by which in a case that the body temperature management file retains a body temperature database of the operator whose body temperature is measured, the display section is caused to display, along with the measured body temperature measurement value, a body temperature graph created on a basis of the body temperature measurement value and latest past body temperature measurement values of measurement performed several times in the past that are accumulated in the body temperature database.

5. The machining center NC operation panel with a body temperature management function according to claim 1, wherein the body temperature acquisition processing unit is configured to have, as the threshold, a first threshold to be compared first with the difference between the body temperature measurement value and the average value, and a second threshold which is greater than the first threshold, and is to be compared next with the difference in a case that the difference is greater than the first threshold, and have a function by which:

in a case that the difference is equal to or smaller than the first threshold, it is assessed that the operator is in a normal body temperature condition;

in a case that the difference is greater than the first threshold, and additionally is equal to or smaller than the second threshold, it is assessed that the operator is in a mild fever condition; and in a case that the difference is greater than the second threshold, it is assessed that the operator is in a severe fever condition that continuation of control should be prohibited immediately.

* * * * *